United States Patent
Sun et al.

(10) Patent No.: US 9,562,027 B2
(45) Date of Patent: Feb. 7, 2017

(54) DEVICE AND METHOD FOR CONTINUOUSLY PREPARING HIGH-PURITY AKD WITHOUT SOLVENT

(71) Applicant: SUZHOU TIANMA SPECIALTY CHEMICALS CO., LTD., Suzhou, Jiangsu (CN)

(72) Inventors: Baochi Sun, Suzhou (CN); Anqi Tan, Suzhou (CN)

(73) Assignee: SUZHOU TIANMA SPECIALTY CHEMICALS CO., LTD., Jiangsu (CN)

( * ) Notice: Subject to any disclaimer, the term of this patent is extended or adjusted under 35 U.S.C. 154(b) by 84 days.

(21) Appl. No.: 14/649,703

(22) PCT Filed: Mar. 12, 2013

(86) PCT No.: PCT/CN2013/072498
§ 371 (c)(1),
(2) Date: Jun. 4, 2015

(87) PCT Pub. No.: WO2014/086122
PCT Pub. Date: Jun. 12, 2014

(65) Prior Publication Data
US 2015/0315163 A1    Nov. 5, 2015

(30) Foreign Application Priority Data

Dec. 4, 2012    (CN) .......................... 2012 1 0513320

(51) Int. Cl.
| | | |
|---|---|---|
| *C07D 305/08* | (2006.01) |
| *B01J 19/18* | (2006.01) |
| *B01J 19/00* | (2006.01) |
| *B01J 19/20* | (2006.01) |
| *C07D 305/12* | (2006.01) |
| *B01F 7/04* | (2006.01) |
| *C07C 45/89* | (2006.01) |
| *C07C 49/88* | (2006.01) |

(52) U.S. Cl.
CPC ............ *C07D 305/08* (2013.01); *B01F 7/048* (2013.01); *B01J 19/0013* (2013.01); *B01J 19/0066* (2013.01); *B01J 19/1806* (2013.01); *B01J 19/1812* (2013.01); *B01J 19/20* (2013.01); *C07C 45/89* (2013.01); *C07C 49/88* (2013.01); *C07D 305/12* (2013.01); *B01J 2219/00076* (2013.01); *B01J 2219/00081* (2013.01); *B01J 2219/00092* (2013.01); *B01J 2219/00094* (2013.01)

(58) Field of Classification Search
CPC .................................................. C07D 305/08
USPC .......................................................... 549/323
See application file for complete search history.

(56) References Cited

U.S. PATENT DOCUMENTS 5,672,721 A * 9/1997 Ettl ..................... C07C 45/89
549/329

FOREIGN PATENT DOCUMENTS

| CN | 2555277 Y | * | 6/2003 |
| CN | 101845030 A | * | 9/2010 |
| CN | 102974295 A | * | 3/2013 |

* cited by examiner

Primary Examiner — Taofiq A Solola
(74) Attorney, Agent, or Firm — Oliff PLC (57) ABSTRACT

Device and method for continuously preparing high-purity AKD without solvent includes a reactor making continuous mixing of raw materials. The process includes: the tertiary amine feeding into the reactor and the continuously feeding acyl chloride from three to ten line; under operating state, the motor rotates the internal cylinder in relation to external cylinder, forcing the fed materials to convey and stir in the conveying section of annular column passage, forcing the materials to shear and mix by movement of shearing and kneading blades. Arrangement of conveying and mixing sections along the axial direction of annular column passage, causes sufficient reaction of materials and controls the material temperature through internal and external heat exchange systems until the reaction products are discharged from outlet. The device and process disperse reaction heat and sufficient material mixture and complete reaction to control the reaction temperature, viscosity and decrease the generation of side reaction.

10 Claims, 4 Drawing Sheets

DEVICE AND METHOD FOR CONTINUOUSLY PREPARING HIGH-PURITY AKD WITHOUT SOLVENT

TECHNICAL FIELD

The present invention relates to a kind of method for continuous preparation of AKD (alkyl or alkylketene dimer), particularly to a kind of method for sufficient mixture and continuous reaction for preparation of high purity AKD through continuous metering of raw material under condition of being free of solvent.

BACKGROUND OF INVENTION

AKD (alkyl or alkylketene dimer) is a kind of sizing agent for paper making. At present, the AKD products manufactured by industrial mass production are acquired by batch production. Along with the growth of market demand, this production method has major limitations and defects such as great quality fluctuation, high labor cost, high consumption of raw materials and energy, etc. Recently, the continuous preparation of AKD has become the development trend of large-scale mass production. Both European patent EP0550107 and Chinese patent CN1596252A disclose the methods for continuous preparation of AKD, but above-mentioned methods continuously feed all of raw materials acyl chloride and tertiary amine according to certain proportion for a single time, which causes the sudden rise of reaction temperature, sharp increase of material viscosity and difficult operation to fail to acquire the high purity products.

Chinese patent CN101845030A also discloses a kind of method for continuous preparation of AKD. This patent applies the specially designed reactor, with main body of conveyor carrying discontinuous propeller blades with fixed stirring rods inserted in the spacing of propeller blades. In two embodiments, one of raw materials tertiary amine is fed for a single time and the other raw material acyl chloride is fed for two times. And the product purity is greatly improved in comparison with control product. Although the iodine value of product could be stable at 43, the iodine value is about 2 less than that of products from batch production and the melting point is about 0.5~10 C lower, which indicates that a lot of impurity exists, the product purity is not high enough and the product quality is not good; if the raw material acyl chloride is fed for three times, the product purity is not obviously improved due to limitation of reactor length, short reaction time and insufficient stirring especially during feeding of last batch of raw materials. The causes affecting the above-mentioned product quality are: (1) under the condition of being free from solvent, the reaction is very fast and even if one of materials acyl chloride is fed through two points, the heat of reaction is released quite concentratively and the reaction temperature is hard to control and the material viscosity is high; (2) this reactor relies on discontinuous propeller blade for shearing and kneading and its structure is simple and axial and radial mixing strength is low with poor self-cleaning capability, so that seizing and wall accretion might occur inside the reactor and the difficult heat dissipation causes the rising of reaction temperature and increasing material viscosity to result in insufficient mixture of materials and finally cause the insufficient dimerization reaction of acyl chloride and tertiary amine and failure of continuous preparation of high purity AKD products. Therefore, the topic of present invention is how to improve the process and device for realization of continuous preparation of high purity AKD products.

DISCLOSURE OF THE INVENTION

The purpose of present invention is to overcome the shortcomings of current technology and provide a set of method for stable and continuous preparation of high purity AKD to meet the demand of industrial mass production.

In order to achieve the above object, the technical proposal adopted by the device for continuous preparation of high purity AKD without solvent in the present invention is: the adopted device includes a kind of reactor which could make continuous mixing reaction of raw materials. The reactor has the axially setup internal cylinder and external cylinder. Under the operating state, the internal cylinder is driven by motor to rotate in relation to external cylinder to form an annular column passage between internal cylinder and external cylinder. The annular column passage is set with conveying section and mixing section along the axial direction and the conveying section and mixing section are arranged one after another along the axial direction of annular column passage. And the conveying section is set with blades to convey and mix the materials and the bottom of blades is fixed to the internal cylinder and the tip of blades is fitted with inner wall of external cylinder; the mixing section is set with shearing blades and kneading blades to shear and mix the materials. The shearing blade consists of supporting block and shearing rod. One end of supporting block is fixed on the internal cylinder and the other end is connected to the shearing rod; one side of shearing rod is fitted with inner wall of external cylinder. The kneading blade consists of support bar and kneading block; one end of support bar is fixed on the external cylinder and the other end is connected to kneading block; one side of kneading block is fitted with outer wall of internal cylinder; the above-mentioned reactor is set with one tertiary amine feeding port, 3-10 acyl chloride feeding ports and one outlet connecting the annular column passage; one tertiary amine feeding port and first acyl chloride feeding port are located at one end of axial direction of annular column passage in reactor, one outlet is located at the other end of axial direction of annular column passage and the other acyl chloride feeding ports are alternatively arranged along the axial direction of annular column passage from the first acyl chloride feeding port; the above-mentioned reactor has two sets of internal and external heat exchange systems, wherein the internal heat exchange system uses the wall of internal cylinder as heat exchange interface and it consists of pipeline, heat exchange medium and inner chamber of internal cylinder; the external heat exchange system uses the wall of external cylinder as heat exchange interface and it consists of pipeline, heat exchange medium and water jacket at outskirt of internal cylinder.

The above described technical solution is explained as follows:

1. In above described technical solution, the mentioned blade could be the helical blade and the mentioned stirring rod is set between the spacing of blades. The stirring rod is of column shape with one end fixed to the external cylinder and the other end fitted with outer wall of internal cylinder.

2. In above described technical solution, the chamber is formed in annular column passage i.e. between internal cylinder and external cylinder. The cross section of annular column passage is of annular space at its cross section in radial direction and it's of thorough column space in axial direction.

3. In above described technical solution, the mentioned supporting block is of block shape with one end fixed to internal cylinder and the other end extended to the inner wall of external cylinder and connected with shearing rod; the mentioned shearing rod is of rod shape with one side fitted with inner wall of external cylinder. Under the operating state of reactor, the internal cylinder is driven by motor to rotate in relation to external cylinder and the shearing rod could scrape off the materials sticking on the inner wall of external cylinder.

4. In above described technical solution, the mentioned support bar is of block shape with one end fixed to external cylinder and the other end extended to the outer wall of internal cylinder and connected with kneading block; the mentioned kneading block is of block shape with one side fitted with outer wall of internal cylinder. Under the operating state of reactor, the internal cylinder is driven by motor to rotate in relation to external cylinder and the kneading block could scrape off the materials sticking on the outer wall of internal cylinder.

5. In above described technical solution, the mentioned internal heat exchange system is equipped with rotating joint, which is connected with inner chamber of internal cylinder.

6. In above described technical solution, the water jacket is fixed on the outer wall of mentioned external cylinder and it consists of outer cover, inner cover, upper end plate, lower end plate, inlet pipe and outlet pipe.

7. In above described technical solution, the mentioned device could be connected by at least two devices with same internal structure in series.

In order to achieve the above object, the technical proposal adopted by the method for continuous preparation of high purity AKD without solvent in the present invention is:

(1) Raw Material

The mentioned raw materials are tertiary amine and acyl chloride;

The applied tertiary amine is:

(I)

In the chemical equation (I), R1, R2 and R3 are C1~C6 alkyl, alkenyl or cycloalkyl.

The applied acyl chloride is:

(II)

In the chemical equation (II), R is C8~C22 alkyl or alkenyl.

(2) Device

The adopted device includes a kind of reactor which could make continuous mixing reaction of raw materials. The reactor has the axially setup internal cylinder and external cylinder. Under the operating state, the internal cylinder is driven by motor to rotate in relation to external cylinder to form an annular column passage between internal cylinder and external cylinder. The annular column passage is set with conveying section and mixing section along the axial direction and the conveying section and mixing section are arranged one after another along the axial direction of annular column passage. And the conveying section is set with blades to convey and mix the materials and the bottom of blades is fixed to the internal cylinder and the tip of blades is fitted with inner wall of external cylinder; the mixing section is set with shearing blades and kneading blades to shear and mix the materials. The shearing blade consists of supporting block and shearing rod. One end of supporting block is fixed on the internal cylinder and the other end is connected to the shearing rod; one side of shearing rod is fitted with inner wall of external cylinder. The kneading blade consists of support bar and kneading block; one end of support bar is fixed on the external cylinder and the other end is connected to kneading block; one side of kneading block is fitted with outer wall of internal cylinder; the above-mentioned reactor is set with one tertiary amine feeding port, 3-10 acyl chloride feeding ports and one outlet connecting the annular column passage; one tertiary amine feeding port and first acyl chloride feeding port are located at one end of axial direction of annular column passage in reactor, one outlet is located at the other end of axial direction of annular column passage and the other acyl chloride feeding ports are alternatively arranged along the axial direction of annular column passage from the first acyl chloride feeding port; the above-mentioned reactor has two sets of internal and external heat exchange systems, wherein the internal heat exchange system uses the wall of internal cylinder as heat exchange interface and it consists of pipeline, heat exchange medium and inner chamber of internal cylinder; the external heat exchange system uses the wall of external cylinder as heat exchange interface and it consists of pipeline, heat exchange medium and water jacket at outskirt of internal cylinder;

(3) Preparation Process

Step 1: Prepare the raw materials required for continuous feeding into reactor according to the mole ratio of 1.05~1.2:1 between tertiary amine and acyl chloride within any unit time and feed the acyl chloride required for continuous feeding into reactor through three to ten lines and the feeding amount of acyl chloride in each line shall be 10~60% of total feeding amount of acyl chloride within any unit time;

Step 2: Use the metering pump to continuously feed the tertiary amine through the mentioned tertiary amine feeding port in reactor according to the requirement of Step 1 and use the metering pump to continuously feed the acyl chloride through the corresponding three to ten acyl chloride feeding ports in three to ten lines according to the requirement of Step 1. Under the operating state of reactor, the main motor drives the internal cylinder to rotate in relation to external cylinder, forcing the fed materials to be conveyed and stirred by blades in the conveying section of annular column passage and forcing the fed materials to be sheared and mixed by relative movement of shearing blades and kneading blades at mixing section of annular column passage. Due to multiple feedings of acyl chloride and alternate arrangement of conveying section and mixing section along the axial direction of annular column passage, it causes the sufficient dimerization reaction of fed materials and gradually moves the materials from feeding ports of reactor to outlet along the annular column passage. During the dimerization reaction process of materials, it uses two sets of internal and external heat exchange systems to control the temperature of materials inside the reactor between 50° C. and 100° C. and control the material viscosity in range of 1~70 Pa·s. The duration period of materials inside the reactor is 5~20 minutes until the reaction products are discharged continuously from outlet;

Step 3: The reaction products discharged continuously from outlet of reactor fall to the continuous extractor. Continuously feed diluted mineral acid solution to continuous extractor for dispersion with reaction products to get the extracted mixing solution, which is finally conveyed to settling basin for separation of oil phase and water phase. The oil phase on the top is molten AKD product and discharged from overflow port of settling basin and the water phase at the bottom is tertiary amine mineral acid solution and discharged from the lower port of settling basin.

The above described technical solution is explained as follows:

1. In above described technical solution, the mentioned tertiary amine could be one of following substances in chemical equation (I): triethylamine; dimethylcyclohexylamine; dimethylisopropylamine. The mentioned acyl chloride could be one of following substances in chemical equation (II): palmitoyl chloride; stearoyl chloride; mixture of palmitoyl chloride and stearoyl chloride in any weight ratio; isostearoyl chloride; mixture of isostearoyl chloride, palmitoyl chloride and stearoyl chloride in any weight ratio.

2. In above described technical solution, the preferred mole ratio of tertiary amine and acyl chloride is 1.06~1.15:1 and the optimal mole ratio of tertiary amine and acyl chloride is 1.08~1.12:1.

3. In above described technical solution, during the Step 2 of mentioned preparation process, preferred temperature of materials in reactor is controlled to be 50~90° C. and the optimal temperature range is 55~85° C.

4. In above described technical solution, after the separation of oil phase and water phase during Step 3 of mentioned preparation process, as the reaction product viscosity prepared by present invention is low, it could be discharged by overflow from top of reactor.

5. In above described technical solution, during Step 3 of mentioned preparation process, the mentioned diluted mineral acid solution could be diluted hydrochloric acid solution or diluted sulphuric acid solution.

6. In above described technical solution, after completion of Step 3 of mentioned preparation process, the AKD by continuous preparation could be directly emulsified to be AKD emulsion; or rinsed, dehydrated and cooled for selling. The tertiary amine mineral acid solution shall be collected for treatment and the tertiary amine could be recycled.

7. In above described technical solution, AKD is dimer of alkyl ketene or alkenyl ketene with structural formula:

Wherein, R is C8~C22 alkyl or alkenyl.

The operating principle of present invention is: the reaction to generate AKD includes the dimerization of acyl chloride dehydrochlorination and neutralization of hydrogen chloride and tertiary amine. The equation of acyl chloride and tertiary amine is:

Under condition of being free from solvent, the characteristic of acyl chloride and tertiary amine reaction is that the reaction is very fast and the heat release is intense, which causes sharp increase of material viscosity to result in difficult control of reaction and insufficient reaction of materials to affect the purity of products. When all materials react concentratively, the material temperature rises sharply and viscosity is far above 100 Pa·s so that the normal stirring and heat transfer are not possible. Relevant researches show that the crystalline forms of tertiary amine hydrochloride are quite different under different conditions. When the solvent is not available, the molar (or slightly excessive amount of tertiary amine) reaction of acyl chloride and tertiary amine could generate the branched long and thin crystal; when the solvent or greatly excessive amount of tertiary amine is available, it will generate the thick and orthorhombic crystal. Under the first scenario, the material viscosity is high and it's difficult to achieve the sufficient mixing effect through mechanical force such as stirring or shearing and the heat of reaction could not be transferred in time, so the temperature is hard to control. Especially the branched long and thin crystal could enclose some unreacted acyl chloride and tertiary amine to have incomplete reaction to lower the product quality. Under the second scenario, due to the availability of solvent or greatly excessive amount of tertiary amine, it improves the reaction condition to generate thicker crystal, greatly lower the material viscosity, reduce the enclosure and entrainment of raw materials, have safer reaction and improve the product purity. However, the solvent recovery process devices are complicated and it increases the energy consumption and environmental pollution; the greatly excessive amount of tertiary amine increases the recovery cost. Neither of two solutions are feasible. The present invention puts forward a novel process operation and special device to solve the problem.

The concept of present invention is to reinforce the mixture of reaction materials under the condition of being free from solvent to make the reactant viscosity controllable on the basis of reactant temperature being controllable to achieve the product quality controllable, i.e. to stable and continuous preparation of high purity AKD. Firstly, continuously feed the tertiary amine (one of raw materials) through the mentioned tertiary amine feeding port in reactor and continuously feed the acyl chloride (the other raw material) through the corresponding three to ten acyl chloride feeding ports of reactor in three to ten lines, i.e. the tertiary amine and a portion of acyl chloride are continuously fed for reaction simultaneously. The tertiary amine is greatly excessive relatively to serve the function of solvent or dilution. Under such environment, the generated amine salt has better crystal form and the enclosure of unreacted material is reduced. Then, continuously feed the acyl chloride through other feeding ports along the length direction of reactor to greatly disperse the heat of reaction to make it easy to control the reaction process.

Secondly, the materials are always sheared and stirred at the conveying section of reactor when the materials are conveyed to achieve the main mixture of materials along the axial direction and the stirring rods in the spacing of blades could scrape off the materials sticking on the wall of internal cylinder to prevent the seizing of materials.

The present invention has another critical element: the mentioned annular column passage is equipped with mixing section in axial direction and the mixing section is equipped with shearing blades and kneading blades to shear and mix the materials. On one side, it forces the sufficient shearing and mixing of fed materials during relative movement of shearing blades and kneading blades in the mixing section of annular column passage to reinforce the mixing of viscous materials in radial direction; on the other side, it realizes the self-cleaning, i.e. the shearing rod on the shearing blade could scrape off the materials sticking on the inner wall of external cylinder to prevent the wall accretion on external cylinder and the kneading block on the kneading blade could scrape off the materials sticking on the outer wall of internal cylinder to prevent the seizing of internal cylinder to reduce the thermal resistance and transfer the heat effectively to increase the opportunity for material reaction and ensure the sufficient detention period.

Thirdly, the heat of reaction generated from the conveying section and mixing section is controlled by the two sets of internal and external heat exchange systems on reactor to further control the temperature of reaction materials.

Due to application of above described technical solution, the present invention has following advantages and effects in comparison with current technology: the application of process of present invention could realize the disperse generation of reaction heat and maintain excellent heat transfer, sufficient material mixture and complete reaction to make it easy to control the reaction temperature and material viscosity, lower the reaction material viscosity 10~70 Pa·s, decrease the generation of side reaction and lower the impurity to ensure the high purity of products.

In above-mentioned Figures: 1. Internal cylinder; 2. External cylinder; 3. Motor; 4. Annular column passage; 5. Conveying section; 6. Blade; 7. Mixing section; 8. Shearing blade; 9. Kneading blade; 10. Supporting block; 11. Shearing rod; 12. Support bar; 13. Kneading block; 14. Tertiary amine feeding port; 15. Acyl chloride feeding port; 16. Outlet; 17. Rotating joint; 18. Stirring rod.

SPECIFIC EMBODIMENT

With reference to the embodiments, the present invention will be described in detail:

Embodiment 1

Device and Method for Continuously Preparing High-Purity AKD without Solvent

The mentioned raw material is triethylamine in tertiary amine, and the acyl chloride is the mixture of palmitoyl chloride and stearoyl chloride, wherein the weight ratio of palmitoyl chloride and stearoyl chloride is 7:13.

Figure 3:
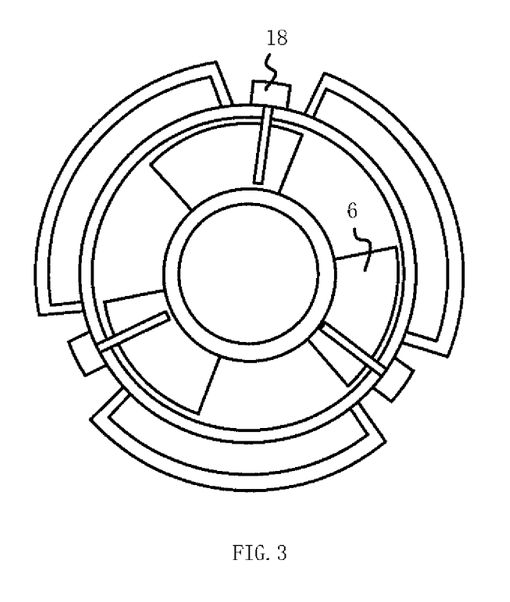
FIG. 3 A-A cross sectional view of FIG. 1.
Figure 4:
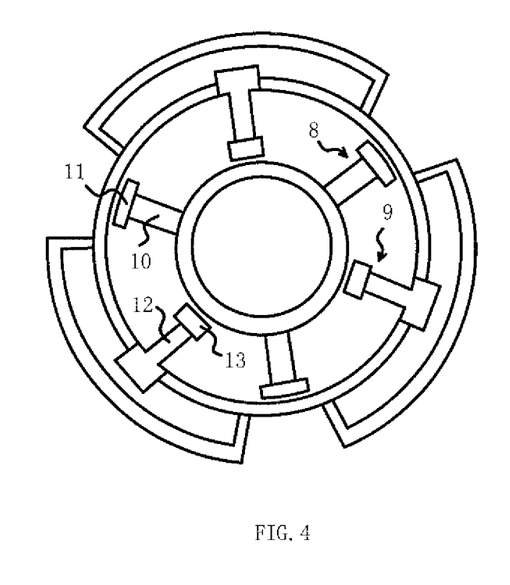
FIG. 4 B-B cross sectional view of FIG. 1.

As shown in FIG. 1 through 5, FIG. 2 shows the internal component shape and arrangement of one conveying section 5 and one mixing section 7 in reactor; FIG. 3 shows the cross sectional view of conveying section 5; and FIG. 4 shows the cross sectional view of mixing section 7. The stainless steel mixing reactor has length of 1800 mm, the diameter of internal cylinder 1 is 133 mm, the diameter of external cylinder 2 is 219 mm, and the internal cylinder 1 and external cylinder 2 are axially setup. Under the operating state, the internal cylinder 1 is driven by motor 3 to rotate in relation to external cylinder 2 to form an annular column passage 4 between internal cylinder 1 and external cylinder 2. The annular column passage 4 is set with three conveying sections 5 and four mixing sections 7 along the axial direction and the conveying sections 5 and mixing sections 7 are arranged one after another along the axial direction of annular column passage 4. And the conveying sections 5 are set with blades 6 to convey and mix the materials. The nominal screw pitch of conveying section is 60 mm and the bottom of blades 6 is fixed to the internal cylinder 1 and the tip of blades 6 is fitted with inner wall of external cylinder 2; the mentioned stirring rod 18 is set between the spacing of blades 6. The mentioned stirring rod 18 is of column shape with one end fixed to the external cylinder 2 and the other end fitted with outer wall of internal cylinder 1. The mixing sections 7 are set with shearing blades 8 and kneading blades 9 to shear and mix the materials. The shearing blade 8 consists of supporting block 10 and shearing rod 11. One end of supporting block 10 is fixed on the internal cylinder 1 and the other end is connected to the shearing rod 11; one side of shearing rod 11 is fitted with inner wall of external cylinder 2. The kneading blade 9 consists of support bar 12 and kneading block 13; one end of support bar 12 is fixed on the external cylinder 2 and the other end is connected to kneading block 13; one side of kneading block 13 is fitted with outer wall of internal cylinder 1. The above-mentioned reactor is set with one tertiary amine feeding port 14 and one acyl chloride feeding port 15 from the starting end, and alternatively set with two acyl chloride feeding ports 15 along the axial direction of annular column passage 4 starting from first acyl chloride feeding port 15 with spacing of 300~500 mm. The materials are pumped in by metering pump through rotameter. The reactor is set with one outlet 16 at its end. The above-mentioned reactor is also equipped with two sets of internal and external heat exchange systems, wherein the internal heat exchange system uses the wall of internal cylinder 1 as heat exchange interface and it consists of pipeline, heat exchange medium and inner chamber of internal cylinder 1 and one end of internal cylinder 1 is connected with rotating joint 17 to form the loop; the external heat exchange system uses the wall of external cylinder 2 as heat exchange interface and it consists of pipeline, heat exchange medium and water jacket at outskirt of internal cylinder 2. The two sets of heat exchange systems are connected and switched with cold and hot medium loops respectively to flexibly control the reaction temperature through adjustment of flow of cold and hot mediums. The number of revolutions of reactor is 60~120 revolutions/minute.

Figure 1:
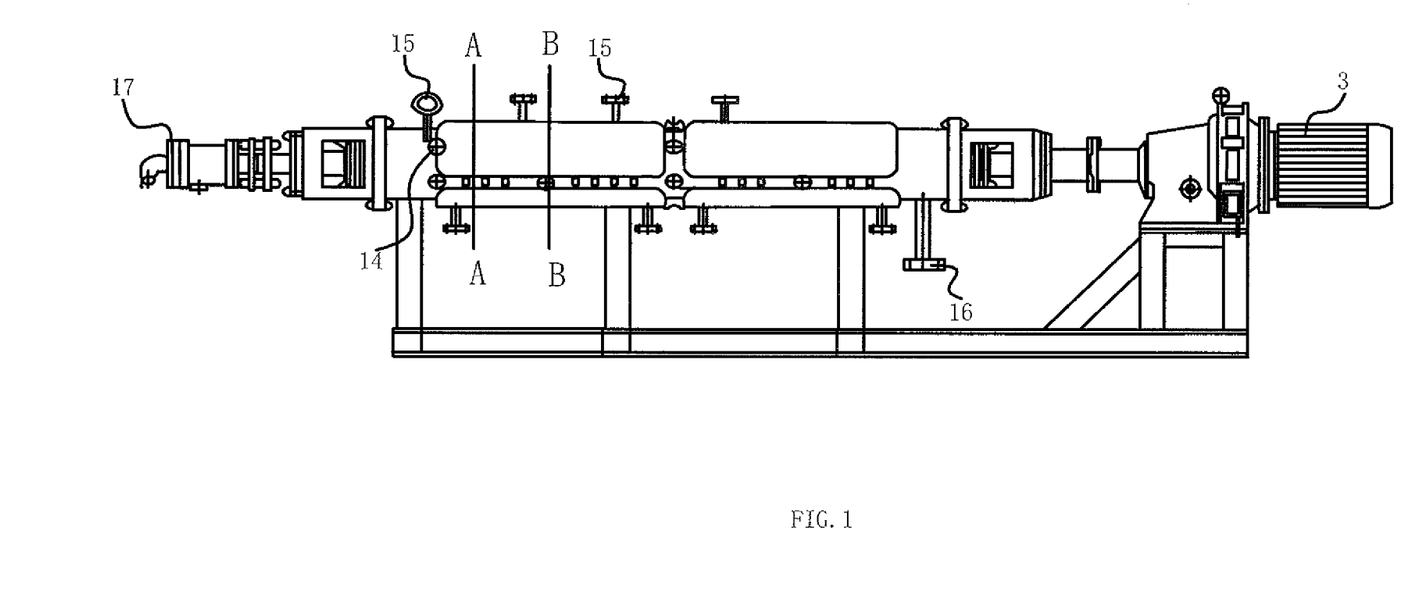
FIG. 1 is front view of overall device structure of present invention.
Figure 2:
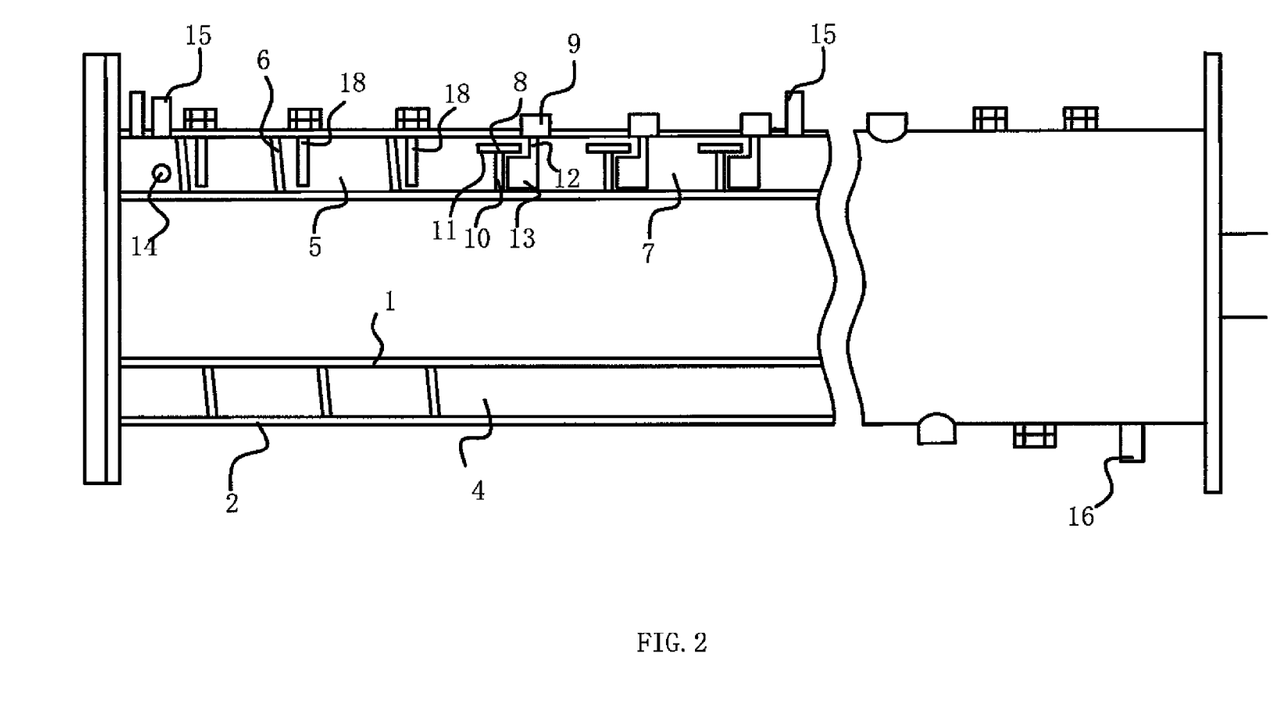
FIG. 2 partial cross sectional view of FIG. 1.
Figure 5:
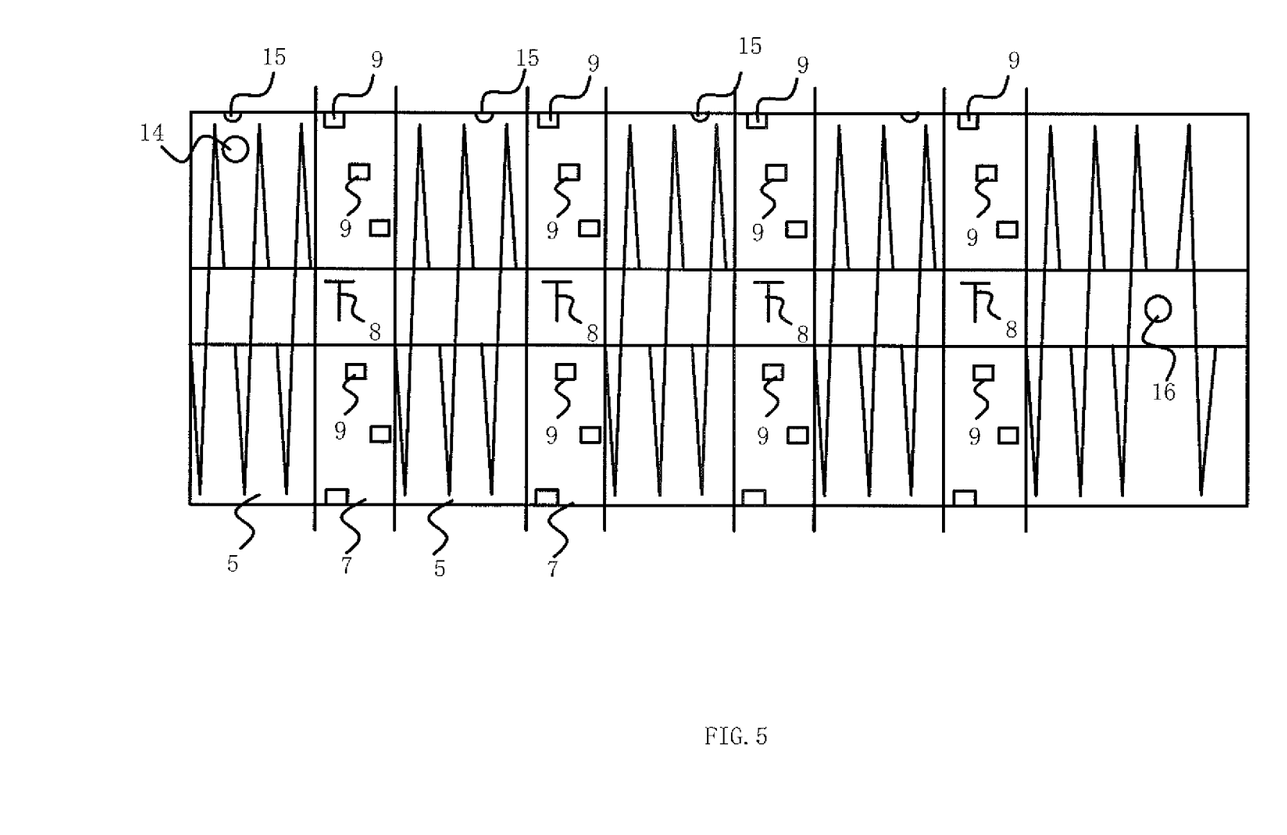
FIG. 5 is schematic of material inlets and outlet and internal components arrangement of FIG. 1.

The reaction products discharged continuously from outlet 16 of reactor are conveyed to the continuous extractor through the pipeline. Continuously feed diluted hydrochloric acid solution to continuous extractor for dispersion with reaction products to get the extracted mixing solution, which is finally conveyed to settling basin for separation of oil phase and water phase. The oil phase on the top is molten AKD product and discharged from overflow port of settling basin and the water phase at the bottom is triethylamine mineral acid solution and discharged from the lower port of settling basin.

When the feeding amount of raw material acyl chloride (weight ratio of palmitoyl chloride and stearoyl chloride is 7:13) is 108 kg/hour, the mole ratio of triethylamine and acyl chloride is 1.05~1.10:1. The feeding proportion of three acyl chloride feeding ports is 5:2.5:2.5. The reactor operates for 17 hours and the highest temperature of reaction materials is about 85° C., the material detention period is about 8 minutes, the material temperature at outlet is about 65° C., the viscosity is 10~70 Pa·s. Take and test 16 samples to get the iodine value of 43.0~44.6 with average value of 43.77 and the melting point of 50.3~50.5° C. The measured melting point is the same as that of batch products.

Embodiment 2

Device and Method for Continuously Preparing High-Purity AKD without Solvent

As shown in FIG. 1 through 5, the mentioned raw material is triethylamine in tertiary amine, and the acyl chloride is the mixture of palmitoyl chloride and stearoyl chloride, wherein the weight ratio of palmitoyl chloride and stearoyl chloride is 13:7. The device, feeding amount and feeding ratio are same as that of Embodiment 1. The reactor operates for 48 hours and take and test 17 batches to get the iodine value of 44.2~46.2 with average value of 45.25 and the melting point of 48.5~49° C. The measured melting point is the same as products prepared with the raw material formulation in batch method.

Embodiment 3

Device and Method for Continuously Preparing High-Purity AKD without Solvent

As shown in FIG. 1 through 5, the stainless steel mixing reactor has length of 3000 mm, the diameter of internal cylinder 1 is 370 mm, the diameter of external cylinder 2 is 530 mm, and the internal cylinder 1 and external cylinder 2 are axially setup. Under the operating state, the internal cylinder 1 is driven by motor 3 to rotate in relation to external cylinder 2 to form an annular column passage 4 between internal cylinder 1 and external cylinder 2. The annular column passage 4 is set with five conveying sections 5 and six mixing sections 7 along the axial direction and the conveying sections 5 and mixing sections 7 are arranged one after another along the axial direction of annular column passage 4. And the conveying sections 5 are set with blades 6 to convey and mix the materials. The nominal screw pitch of conveying section is 120 mm and the bottom of blades 6 is fixed to the internal cylinder 1 and the tip of blades 6 is fitted with inner wall of external cylinder 2; the mentioned stirring rod 18 is set between the spacing of blades 6. The mentioned stirring rod 18 is of column shape with one end fixed to the external cylinder 2 and the other end fitted with outer wall of internal cylinder 1. The mixing sections 7 are set with shearing blades 8 and kneading blades 9 to shear and mix the materials. The shearing blade 8 consists of supporting block 10 and shearing rod 11. One end of supporting block 10 is fixed on the internal cylinder 1 and the other end is connected to the shearing rod 11; one side of shearing rod 11 is fitted with inner wall of external cylinder 2. The kneading blade 9 consists of support bar 12 and kneading block 13; one end of support bar 12 is fixed on the external cylinder 2 and the other end is connected to kneading block 13; one side of kneading block 13 is fitted with outer wall of internal cylinder 1. The above-mentioned reactor is set with one tertiary amine feeding port 14 and one acyl chloride feeding port 15 from the starting end, and alternatively set with three acyl chloride feeding ports 15 along the axial direction of annular column passage 4 starting from first acyl chloride feeding port 15 with spacing of 300~500 mm. The materials are pumped in by metering pump through rotameter. The reactor is set with one outlet 16 at its end. The above-mentioned reactor is also equipped with two sets of internal and external heat exchange systems, wherein the internal heat exchange system uses the wall of internal cylinder 1 as heat exchange interface and it consists of pipeline, heat exchange medium and inner chamber of internal cylinder 1 and one end of internal cylinder 1 is connected with rotating joint 17 to form the loop; the external heat exchange system uses the wall of external cylinder 2 as heat exchange interface and it consists of pipeline, heat exchange medium and water jacket at outskirt of internal cylinder 2. The two sets of heat exchange systems are connected and switched with cold and hot medium loops respectively to flexibly control the reaction temperature through adjustment of flow of cold and hot mediums. The number of revolutions of reactor is 4560 revolutions/minute.

When the feeding amount of raw material acyl chloride (weight ratio of palmitoyl chloride and stearoyl chloride is 13:7) is 540 kg/hour, the mole ratio of triethylamine and acyl chloride is 1.05~1.10:1. The feeding amount of first acyl chloride feeding port is 50% of total amount and the other 50% is fed through other three feeding ports respectively. The reactor operates for 6 hours and the highest temperature of reaction materials is about 85° C., the material detention period is about 10 minutes, the material temperature at outlet is about 60~65° C., the viscosity is 10~65 Pa·s. Take and test five batches to get the iodine value of 45.3~46.0 with average value of 45.7.

Embodiment 4

Device and Method for Continuously Preparing High-Purity AKD without Solvent

As shown in FIG. 1 through 5, the mentioned raw material is dimethylcyclohexylamine in tertiary amine, and the acyl chloride is the isostearoyl chloride and mixture of palmitoyl chloride and stearoyl chloride, wherein the weight ratio of isostearoyl chloride and mixture of palmitoyl chloride and stearoyl chloride is 4:6 and the weight ratio of palmitoyl chloride and stearoyl chloride is 7:13. The device, feeding amount and feeding ratio are same as that of Embodiment 3. The reactor operates for 24 hours. Take and test ten batches to get the iodine value of 44.0~45.9 with average value of 44.9.

Comparative Example 1

The reactor's diameter is 219 mm and effective length is 1400 mm. It's a reactor equipped with mixing section, but without conveying section. The conveying section is set with blades to convey and mix the materials and the stirring rod is set between the spacing of blades. The feeding amount of raw material acyl chloride (weight ratio of palmitoyl chloride and stearoyl chloride is 13:7) is 108 kg/hour, the mole ratio of triethylamine and acyl chloride is 1.05~1.10:1 and all materials are continuously fed from starting end respectively. The reactor operates for 24 hours and the average iodine value is 40.8.

Comparative Example 2

The device and material formula are same as that of comparative example 1 and the mixing section is not available. The difference is that the acyl chloride is fed into reactor from two points (ratio is 7:3) and maximum material temperature is 115° C. The reactor operates for 144 hours and the average iodine value is 44.35, the melting point is 47.0~48.8° C., which is 1° C. lower than that of products in batch method on average.

Comparative Example 3

The device, material formular, ratio and feeding amount as same as that of embodiment 1. The difference is the acyl chloride is fed into reactor from two points (ratio is 7:3) and maximum material temperature is 94° C., and the reactor operates for 5 hours. The average iodine value is 42.0 and the melting point is 50.3° C., which is same as that of products in batch method.

In the above-mentioned embodiment and comparative example, the iodine value is a kind of index for degree of unsaturation of organic compound and an index to measure the AKD purity. The higher the measured iodine value is, the higher purity of AKD is. Furthermore, in the embodiment of present invention, the raw material tertiary amine could be triethylamine, dimethylcyclohexylamine and dimethylisopropylamine and the raw material acyl chloride could be mixture of palmitoyl chloride and stearoyl chloride and the mixture of isostearoyl chloride, palmitoyl chloride and stearoyl chloride, but the those skilled in the art shall easily understand the same or similar effect could be achieved when the materials tertiary amine and acyl chloride beyond the range of disclosed formula range of present invention but meeting the requirement of chemical equation (I) and (II) vary to some extent.

It's known from the embodiments and comparative examples that the specific process and devices proposed by present invention could control the reaction process well, reduce the material temperature and viscosity and reduce the side reaction to acquire the stable high purity product on the condition of being free from solvent.

It should be noted that the above described embodiments are only for illustration of technical concept and characteristics of present invention with purpose of making those skilled in the art understand the present invention, and thus these embodiments shall not limit the protection range of present invention. The equivalent changes or modifications according to spiritual essence of present invention shall fall in the protection scope of present invention.

The invention claimed is:

1. A kind of device for continuous preparation of high purity AKD without solvent, wherein:
the adopted device includes a kind of reactor which could make continuous mixing reaction of raw materials; the reactor has the axially setup internal cylinder and external cylinder; under the operating state, the internal cylinder is driven by motor to rotate in relation to external cylinder to form an annular column passage between internal cylinder and external cylinder; the annular column passage is set with conveying section and mixing section along the axial direction and the conveying section and mixing section are arranged one after another along the axial direction of annular column passage; and the conveying section is set with blades to convey and mix the materials and the bottom of blades is fixed to the internal cylinder and the tip of blades is fitted with inner wall of external cylinder; the mixing section is set with shearing blades and kneading blades to shear and mix the materials; the shearing blade consists of supporting block and shearing rod; one end of supporting block is fixed on the internal cylinder and the other end is connected to the shearing rod; one side of shearing rod is fitted with inner wall of external cylinder; the kneading blade consists of support bar and kneading block; one end of support bar is fixed on the external cylinder and the other end is connected to kneading block; one side of kneading block is fitted with outer wall of internal cylinder; the above-mentioned reactor is set with one tertiary amine feeding port, 3-10 acyl chloride feeding ports and one outlet connecting the annular column passage; one tertiary amine feeding port and first acyl chloride feeding port are located at one end of axial direction of annular column passage in reactor, one outlet is located at the other end of axial direction of annular column passage and the other acyl chloride feeding ports are alternatively arranged along the axial direction of annular column passage from the first acyl chloride feeding port; the above-mentioned reactor has two sets of internal and external heat exchange systems, wherein the internal heat exchange system uses the wall of internal cylinder as heat exchange interface and it consists of pipeline, heat exchange medium and inner chamber of internal cylinder; the external heat exchange system uses the wall of external cylinder as heat exchange interface and it consists of pipeline, heat exchange medium and water jacket at outskirt of internal cylinder.

2. A kind of device for continuous preparation of high purity AKD without solvent according to claim 1, wherein: the mentioned blade could be the helical blade and the mentioned stirring rod is set between the spacing of blades, the stirring rod is of column shape with one end fixed to the external cylinder and the other end fitted with outer wall of internal cylinder.

3. A kind of device for continuous preparation of high purity AKD without solvent according to claim 1, wherein: the mentioned internal heat exchange system is equipped with rotating joint, which is connected with inner chamber of internal cylinder.

4. A kind of method for continuous preparation of high purity AKD without solvent, wherein:
the mentioned raw materials are tertiary amine and acyl chloride;
the applied tertiary amine is:

in the chemical equation (I), R1, R2 and R3 are C1~C6 alkyl, alkenyl or cycloalkyl;
the applied acyl chloride is:

(II)

in the chemical equation (II), R is C8~C22 alkyl or alkenyl;

the adopted device includes a kind of reactor which could make continuous mixing reaction of raw materials; the reactor has the axially setup internal cylinder and external cylinder; under the operating state, the internal cylinder is driven by motor to rotate in relation to external cylinder to form an annular column passage between internal cylinder and external cylinder; the annular column passage is set with conveying section and mixing section along the axial direction and the conveying section and mixing section are arranged one after another along the axial direction of annular column passage; and the conveying section is set with blades to convey and mix the materials and the bottom of blades is fixed to the internal cylinder and the tip of blades is fitted with inner wall of external cylinder; the mixing section is set with shearing blades and kneading blades to shear and mix the materials; the shearing blade consists of supporting block and shearing rod; one end of supporting block is fixed on the internal cylinder and the other end is connected to the shearing rod; one side of shearing rod is fitted with inner wall of external cylinder; the kneading blade consists of support bar and kneading block; one end of support bar is fixed on the external cylinder and the other end is connected to kneading block; one side of kneading block is fitted with outer wall of internal cylinder, the above-mentioned reactor is set with one tertiary amine feeding port, 3-10 acyl chloride feeding ports and one outlet connecting the annular column passage; one tertiary amine feeding port and first acyl chloride feeding port are located at one end of axial direction of annular column passage in reactor, one outlet is located at the other end of axial direction of annular column passage and the other acyl chloride feeding ports are alternatively arranged along the axial direction of annular column passage from the first acyl chloride feeding port; the above-mentioned reactor has two sets of internal and external heat exchange systems, wherein the internal heat exchange system uses the wall of internal cylinder as heat exchange interface and it consists of pipeline, heat exchange medium and inner chamber of internal cylinder; the external heat exchange system uses the wall of external cylinder as heat exchange interface and it consists of pipeline, heat exchange medium and water jacket at outskirt of internal cylinder, wherein the preparation process includes;

Step 1: Prepare the raw materials required for continuous feeding into reactor according to the mole ratio of 1.05~1.2:1 between tertiary amine and acyl chloride within any unit time and feed the acyl chloride required for continuous feeding into reactor through three to ten lines and the feeding amount of acyl chloride in each line shall be 10~60% of total feeding amount of acyl chloride within any unit time;

Step 2: Use the metering pump to continuously feed the tertiary amine through the mentioned tertiary amine feeding port in reactor according to the requirement of Step 1 and use the metering pump to continuously feed the acyl chloride through the corresponding three to ten acyl chloride feeding ports in three to ten lines according to the requirement of Step 1; under the operating state of reactor, the main motor drives the internal cylinder to rotate in relation to external cylinder, forcing the fed materials to be conveyed and stirred by blades in the conveying section of annular column passage and forcing the fed materials to be sheared and mixed by relative movement of shearing blades and kneading blades at mixing section of annular column passage; due to multiple feedings of acyl chloride and alternate arrangement of conveying section and mixing section along the axial direction of annular column passage, it causes the sufficient dimerization reaction of fed materials and gradually moves the materials from feeding ports of reactor to outlet along the annular column passage; during the dimerization reaction process of materials, it uses two sets of internal and external heat exchange systems to control the temperature of materials inside the reactor between 50° C. and 100° C. and control the material viscosity in range of 1~70 Pa·s; the duration period of materials inside the reactor is 5~20 minutes until the reaction products are discharged continuously from outlet;

Step 3: The reaction products discharged continuously from outlet of reactor fall to the continuous extractor; continuously feed diluted mineral acid solution to continuous extractor for dispersion with reaction products to get the extracted mixing solution, which is finally conveyed to settling basin for separation of oil phase and water phase; the oil phase on the top is molten AKD product and discharged from overflow port of settling basin and the water phase at the bottom is tertiary amine mineral acid solution and discharged from the lower port of settling basin.

5. A kind of method for continuous preparation of high purity AKD without solvent according to claim 4, wherein: the mentioned tertiary amine could be one of following substances in chemical equation (I):

Triethylamine;
Dimethylcyclohexylamine;
Dimethylisopropylamine;
the mentioned acyl chloride could be one of following substances in chemical equation (II):
Palmitoyl chloride;
Stearoyl chloride;
mixture of palmitoyl chloride and stearoyl chloride in any weight ratio;
Isostearoyl chloride;
mixture of isostearoyl chloride, palmitoyl chloride and stearoyl chloride in any weight ratio.

6. A kind of method for continuous preparation of high purity AKD without solvent according to claim 4, wherein: the mole ratio of mentioned tertiary amine and acyl chloride is 1.06~1.15:1.

7. A kind of method for continuous preparation of high purity AKD without solvent according to claim 6, wherein: the mole ratio of mentioned tertiary amine and acyl chloride is 1.08~1.12:1.

8. A kind of method for continuous preparation of high purity AKD without solvent according to claim 4, wherein: during Step 2 of mentioned preparation process, the material temperature in reactor is controlled to be 50~90° C.

9. A kind of method for continuous preparation of high purity AKD without solvent according to claim 8, wherein: during Step 2 of mentioned preparation process, the material temperature in reactor is controlled to be 55~85° C.

10. A kind of method for continuous preparation of high purity AKD without solvent according to claim 4, wherein: during Step 3 of mentioned preparation process, the mentioned diluted mineral acid solution is diluted hydrochloric acid solution or diluted sulphuric acid solution.

* * * * *